United States Patent [19] [11] Patent Number: 4,766,037
Watanabe et al. [45] Date of Patent: Aug. 23, 1988

[54] PHOTODEGRADABLE MICROCAPSULES

[75] Inventors: Akio Watanabe; Shintaro Washizu; Fumiaki Shinozaki, all of Shizuoka; Shun-ichi Ishikawa; Toshiaki Aoai, both of Kanagawa, all of Japan

[73] Assignee: Fuji Photo Film Co., Ltd., Kanagawa, Japan

[21] Appl. No.: 906,702

[22] Filed: Sep. 9, 1986

[30] Foreign Application Priority Data

Sep. 9, 1985 [JP] Japan ................................ 60-198744
Sep. 9, 1985 [JP] Japan ................................ 60-198745

[51] Int. Cl.$^4$ ...................... B01J 13/02; B32B 27/34; G03C 1/72
[52] U.S. Cl. ............................... 428/402.21; 264/4.7; 424/462; 424/497; 428/321.5; 430/138
[58] Field of Search ................ 264/4.7; 428/402.21; 424/462, 497; 430/138

[56] References Cited

U.S. PATENT DOCUMENTS

| 3,173,878 | 3/1965 | Reyes | 264/4.6 |
| 3,551,346 | 12/1970 | Breen et al. | 264/4.7 X |
| 3,730,905 | 5/1973 | Koerner et al. | 264/4.7 X |
| 3,839,047 | 10/1974 | Suga et al. | 430/138 |
| 4,508,807 | 4/1985 | Adair | 430/138 |

Primary Examiner—Richard D. Lovering
Attorney, Agent, or Firm—Sughrue, Mion, Zinn, Macpeak, and Seas

[57] ABSTRACT

A photodegradable microcapsule is described which has a wall made of a polymer coat having an acid-decomposable bond selected from a silylether bond and a silylureido bond and which contains a compound that generates an acid upon light irradiation.

1 Claim, No Drawings

PHOTODEGRADABLE MICROCAPSULES

FIELD OF THE INVENTION

The present invention relates to photodegradable microcapsules and, more particularly, to microcapsules wherein a liquid of semisolid material containing a compound which generates an acid under illumination is encapsulated with a synthetic polymer coat having a silylether or silylureido bond. The present invention also relates to microcapsules prepared by interfacial polycondensation or in situ polymerization using as one component of the capsule wall a monomer which has or forms a silylether or silylureido group. Further, in addition, the present invention relates to microcapsules that contain a light-activated acid generator which, under illumination, generates an acid and decomposes the silylether or silylureido bonds in the capsule wall, thereby causing light-initiated disintegration of the wall or changes in its characteristics.

BACKGROUND OF THE INVENTION

Heretofore, microcapsules have been prepared by a method that utilizes the phenomenon of coacervation of gelatin and gum arabic; a method that depends on the interfacial polycondensation of a polyisocyanate and a polyamine, a polyisocyanate and a polyol, or a polybasic acid chloride and a polyamine, or a method which involves the in situ polymerization of a polyisocyanate and a polyol, polymerization of styrene monomers, or the in situ polymerization of melamine- or ureaformaldehyde. These prior art microcapsules are simply intended to protect the confined core material or expose it by rupturing the capsules under pressure. It suffices that the capsule wall satisfies the following physical requirements: the wall normally prevents the liquid core material from going out of the capsule but can be ruptured under pressure to permit the exposure of the core material as required; or the thickness and the porosity of the wall are so controlled that it permits gradual release of the core material. In order to meet these requirements, various materials have been reviewed with regard to their use as microcapsule walls and many types of microcapsules have been prepared by interfacial polycondensation or in situ polymerization which is intended to make capsule walls of polyesters, polyamides, polyurethane, polyurea, urea/formaldehyde resin or melamine/formaldehyde resin.

Attempts have also been made to prepare light- or heat-sensitive microcapsules which contain materials that are decomposed by light or heat to generate gases which break the capsule wall to permit the exposure of the core material.

SUMMARY OF THE INVENTION

According to one aspect, the present invention provides a photodegradable microcapsule that has a wall made of a polymer coat having a silylether bond that is capable of decomposition by an acid and which contains a compound that generates an acid under irradiation.

According to another aspect, the present invention provides a photodegradable microcapsule that has a wall made of a polymer coat having a silylureido bond that is capable of decomposition by an acid and which contains a compound that generates an acid under irradiation.

DETAILED DESCRIPTION OF THE INVENTION

The present invention relates to a novel microcapsule using a wall that is possessed of unconventional new capabilities. One great feature of the present invention is that an acid generator which generates an acid under irradiation is confined in the capsule and, under irradiation, an acid is generated to cause a change in the physical properties of the capsule wall. The prior art microcapsule is simply intended to expose the core material by rupturing the capsule wall under pressure. According to the present invention, the microcapsule wall itself is disintegrated or its characteristics are greatly changed upon irradiation by light, bringing about one of the following effects: the confined core material can be readily recovered after irradiation by light; the wall being irradiated becomes readily rupturable under a very small pressure; the core becomes readily releasable upon application of heat; a liquid component around the capsule can permeate into the capsule through the wall simply by irradiation; or an external molten composition can readily enter into the capsule upon application of heat. Therefore, the present invention relates to a microcapsule that has the ability to exhibit entirely new features by the action of light.

The microcapsule according to the first aspect of the present invention is characterized by using a capsule wall which is formed of a polymer coat having a silylether group that is represented by the following formula (I) and which is capable of decomposition by an acid:

(I)

A compound having this silylether group is readily decomposed by an acid which is generated under irradiation. The process of this decomposition may be illustrated by the following scheme (II):

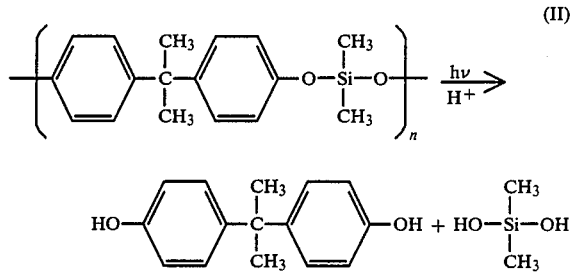
(II)

The microcapsule of the present invention may be prepared by one of the following methods, selection of which depends upon the material of which the capsule wall is formed: interfacial polymerization, wherein two wall-forming materials, one being present in an organic phase and the other in an aqueous phase, are caused to enter into a polymerization reaction at the interface between the organic and aqueous phases so as to form a microcapsule; or in situ polymerization, wherein a microcapsule is formed from two wall-forming materials which are dissolved or present only in an organic phase. A microcapsule having silylether group is formed by reaction between two or more compounds having two or more functional groups which will react with each other to form a polymer.

Typical examples of the wall-forming materials that may be used in the first aspect of the present invention are shown in Table 1.

TABLE 1

| A | B |
|---|---|
| Polyisocyanate compound | $R_{(4-n)}$—Si—$(OR_1'$—OH$)_n$ or $R_1''$—[Si—$(OR_1'$—OH$)_m R_{(3-m)}]_n$ $n = 2, 3, 4; m = 1, 2, 3$ |
| $R_{(4-n)}$—Si—$(Cl)_n$ or $R_1'$—[Si—$(Cl)_m R_{(3-m)}]_n$ $n = 2, 3, 4; m = 1, 2, 3$ | Polyhydric alcohol |
| $R_{(4-n)}$—Si—$(OR_1'OCONHR_1''$—$NCO_x)_n$ or $R_1'''$—[Si—$(OR_1'OCONHR_1''$—$NCO_x)_m R_{(3-m)}]_n$ $n = 2, 3, 4; x = 1, 2, 3;$ $m = 1, 2, 3$ | Polyamine |
| $R_{(4-n)}$—Si—$(OR_1'OCONHR_1''$—$NCO_x)_n$ or $R_1'''$—[Si—$(OR_1'OCONHR_1''$—$NCO_x)_m R_{(3-m)}]_n$ $n = 2, 3, 4; x = 1, 2, 3;$ $m = 1, 2, 3$ | Water |
| $R_{(4-n)}$—Si—$(OR_1'OCONHR_1''$—$NCO_x)_n$ or $R_1'''$—[Si—$(OR_1'OCONHR_1''$—$NCO_x)_m R_{(3-m)}]_n$ $n = 2, 3, 4; x = 1, 2, 3;$ $m = 1, 2, 3$ | Polyhydric alcohol |
| $(R_1''''O)_n$—Si—$(NCO)_{(4-n)}$ $n = 1, 2$ | Water |
| $(R_1''''O)_n$—Si—$(NCO)_{(4-n)}$ $n = 1, 2$ | Polyamine |
| Polybasic acid chloride | $R_{(4-n)}$—Si—$(OR_1'OH)_n$ or $R_1''$—[Si—$(OR_1'$—OH$)_m R_{(3-m)}]_n$ $n = 2, 3, 4; m = 1, 2, 3$ |
| Polyisocyanate compound | $R_{(4-n)}$—Si—$(OR_1'$—$NH_2)_n$ or $R_1''$—[Si—$(OR_1'$—$NH_2)_m R_{(3-m)}]_n$ $n = 2, 3, 4; m = 1, 2, 3$ |
| Polybasic acid chloride | $R_{(4-n)}$—Si—$(O$—$R_1'$—$NH_2)_n$ or $R_1''$—[Si—$(OR_1'$—$NH_2)_m R_{(3-m)}]_n$ $n = 2, 3, 4; m = 1, 2, 3$ |

The symbols used in Table 1 have the following meanings: R is a hydrogen atom, an alkyl group, an alkenyl group, an aryl group, an aralkyl group, an alkoxy group or an aryloxy group; $R_1'$ is a divalent aliphatic or aromatic hydrocarbon group which may have a substituent; $R_1''$ is a di- to tetravalent aliphatic or aromatic hydrocarbon group which may have a substituent; $R_1'''$ is an n-valent aliphatic or aromatic hydrocarbon group which may have a substituent; and $R_1''''$ is an optionally substituted alkyl, aryl or aralkyl group.

The substituents defined above include a halogen atom, an alkyl group, an aryl group, an alkoxy group, an acyl group, an alkoxycarbonyl group, an acylamino group, an alkylamino group, a carbamoyl group, a nitro group, a cyano group, a sulfamoyl group, a carboxyl group, and the like.

The microcapsule according to the second aspect of the present invention is characterized by using a capsule wall which is formed of a polymer coat having a silylureido group that is represented by the following formula (III) and which is capable of decomposition by an acid:

(III)

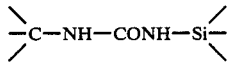

A compound having this silylureido group is readily decomposed by an acid that is generated under irradiation, as illustrated by the following scheme:

(IV)

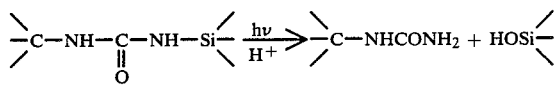

The microcapsule according to the second aspect of the present invention may be prepared by one of the following methods, selection of which depends upon the material of which the capsule wall is formed: encapsulation by interfacial polymerization wherein two wall-forming materials, one being present in an organic phase and the other in an aqueous phase, are caused to enter into a polymerization reaction at the interface between the organic and aqueous phases so as to form a microcapsule; or encapsulation by in situ polymerization wherein a microcapsule is formed from two wall-forming materials which are dissolved or present only in an organic phase. A microcapsule having a silylureido group is formed by reaction between two or more compounds having two or more functional groups which will react with each other to form a polymer.

Typical examples of the wall-forming materials that may be used in the second aspect of the present invention are shown in Table 2.

TABLE 2

| A | B |
|---|---|
| Polyisocyanate compound | $R_{(4-n)}'$—Si—$(NHCONHR_2'$—OH$)_n$ or $R_2''$—[Si—$(NHCONHR_2'$—OH$)_m R_{(3-m)}']_n$ $n = 2, 3, 4; m = 1, 2, 3$ |

TABLE 2-continued

| A | B |
| --- | --- |
| $R_{(4-n)}'$—Si—$(Cl)_n$ or $R_2'$—[Si—$(Cl)_m R_{(3-m)}]_n$ $n = 2, 3, 4; m = 1, 2, 3$ | $R_{(4-n)}'$—Si—$(NHCONHR_2'OH)_n$ or $R_2''$—[Si—$(NHCONHR_2'OH)_m R_{(3-m)}']_n$ $n = 2, 3, 4; m = 1, 2, 3$ |
| $R_{(4-n)}'$—Si—$(NHCONHR_2'OCONHR_2''$—$NCO_x)_n$ or $R_2'''$—[Si—$(NHCONHR_2'OCONHR_2''$—$NCO_x)_m R_{(3-m)}']_n$ $x = 1, 2, 3; n = 2, 3, 4; m = 1, 2, 3$ | Polyamine |
| $R_{(4-n)}'$—Si—$(NHCONHR_2'OCONHR_2''$—$NCO_x)_n$ or $R_2'''$—[Si—$(NHCONHR_2'OCONHR_2''$—$NCO_x)_m R_{(3-m)}']_n$ $n = 2, 3, 4; x = 1, 2, 3; m = 1, 2, 3$ | Water |
| $R_{(4-n)}'$—Si—$(NHCONHR_2'OCONHR_2''$—$NCO_x)_n$ or $R_2'''$—[Si—$(NHCONHR_2'OCONHR_2''$—$NCO_x)_m R_{(3-m)}']_n$ $x = 1, 2, 3; n = 2, 3, 4; m = 1, 2, 3$ | Polyhydric alcohol |
| $R_4'$—Si—$(NCO)_{(4-n)}$ $n = 1, 2$ | Polyhydric alcohol |
| $R_4'$—Si—$(NCO)_{(4-n)}$ $n = 1, 2$ | Polyamine |
| Polybasic acid chloride | $R_{(4-n)}'$—Si—$(NHCONHR_2'OH)_n$ or $R_2''$—[Si—$(NHCONHR_2'$—$OH)_m R_{(3-m)}']_n$ $n = 2, 3, 4; m = 1, 2, 3$ |
| Polyisocyanate compound | $R_{(4-n)}'$—Si—$(NHCONHR_2'$—$NH_2)_n$ or $R_2''$—[Si—$(NHCONHR_2'$—$NH_2)_m R_{(3-m)}']_n$ $n = 2, 3, 4; m = 1, 2, 3$ |
| Polybasic acid chloride | $R_{(4-n)}'$—Si—$(NHCONHR_2'$—$NH_2)_n$ or $R_2''$—[Si—$(NHCONHR_2'$—$NH_2)_m R_{(3-m)}']_n$ $n = 2, 3, 4; m = 1, 2, 3$ |

The symbols used in Table 2 have the following meanings: R' is a hydrogen atom, an alkyl group, an alkenyl group, an aryl group, an aralkyl group, an alioxy group or an aryloxy group; $R_2'$ is a divalent aliphatic or aromatic hydrocarbon group which may have a substituent; $R_2''$ is a di- to tetravalent aliphatic or aromatic hydrocarbon group which may have a substituent; and $R_2'''$ is an n-valent aliphatic or aromatic hydrocarbon group which may have a substituent.

The substituents defined above include a halogen atom, an alkyl group, an aryl group, an alkoxy group, an acyl group, an alkoxycarbonyl group, an acylamino group, an alkylamino group, a carbamoyl group, a nitro group, a cyano group, a sulfamoyl group, a carboxyl group, and the like.

Specific examples of the polyisocyanates that may be used in the present invention are listed below: diisocyanates such as m-phenylene diisocyanate, p-phenylene diisocyanate, 2,6-tolylene diisocyanate, 2,4-tolylene diisocyanate, naphthalene-1,4-diisocyanate, diphenylmethane-4,4'-diisocyanate, 3,3'-dimethoxy-4,4'-biphenyl diisocyanate, 3,3'-dimethyldiphenylmethane-4,4'-diisocyanate, xylylene-1,4-diisocyanate, 4,4'-diphenylpropane diisocyanate, trimethylene diisocyanate, hexamethylene diisocyanate, propylene-1,2-diisocyanate, butylene-1,2-diisocyanate, cyclohexylene-1,2-diisocyanate and cyclohexylene-1,4-diisocyanate; diisothiocyanates such as p-phenylene diisothiocyanate, xylylene-1,4-diisothiocyanate and ethylidene diisothiocyanate; triisocyanates such as 4,4',4''-triphenylmethane triisocyanate and toluene-2,4,6-triisocyanate; tetraisocyanates such as 4,4'-dimethyldiphenylmethane and 2,2',5,5'-tetraisocyanate; and isocyanate prepolymers such as the addition product of hexamethylene diisocyanate and hexanetriol, the addition product of 2,4-tolylene diisocyanate and pyrocatechol, the addition product of tolylene diisocyanate and hexanetriol, the addition product of tolylene diisocyanate and trimethylolpropane, and the addition product of xylylene diisocyanate and trimethylolpropane.

Illustrative polyhydric alcohols include aliphatic or aromatic polyhydric alcohols, hydroxypolyesters and hydroxypolyalkylene ethers, which are exemplified by the following: aromatic and aliphatic polyhydric alcohols such as catechol, resorcinol, hydroquinone, 1,2-dihydroxy-4-methylbenzene, 1,3-dihydroxy-5-methylbenzene, 3,4-dihydroxy-1-methylbenzene, 3,5-dihydroxy-1-methylbenzene, 2,4-dihydroxyethylbenzene, 1,3-naphthalenediol, 1,5-naphthalenediol, 2,7-naphthalenediol, 2,3-naphthalenediol, o,o'-biphenol, p,p'-biphenol, 1,1'-bis-2-naphthol, bisphenol A, 2,2'-bis(4-hydroxyphenyl)butane, 2,2'-bis(4-hydroxyphenyl)isopentane, 1,1'-(4-hydroxyphenyl)cyclopentane, 1,1'-bis(4-hydroxyphenyl)cyclohexane, 2,2'-bis(4-hydroxy-3-methylphenyl)propane, bis(2-hydroxyphenyl)methane, xylylenediol, ethylene glycol, 1,3-propylene glycol, 1,4-butylene glycol, 1,5-pentanediol, 1,6-heptanediol, 1,7-heptanediol, 1,8-octanediol, 1,1,1-trimethylolpropane, hexanetriol, pentaerythritol, glycerin, and sorbitol; hydroxypolyesters prepared from polyvalent carboxylic acids and polyhydric alcohols; and hydroxypolyalkylene ethers which are the condensation products of alkylene oxides and polyhydric alcohols.

Particularly useful hydroxypolyalkylene ethers are those which are prepared from highly lipophilic alkylene oxides having 3 to 6 carbon atoms, such as polyethers which are the condensation products of polypropylene oxide or polybutylene oxide and glycol, glycerin, pentaerythritol or sorbitol.

Illustrative polyamines include aromatic polyamines such as o-phenylenediamine, p-phenylenediamine, 1,5-diaminonaphthalene and phthalamide; and aliphatic polyamines such as N,N'-1,3-propylenediamine, N,N'-1,4-butylenediamine, and hexamethylenediamine. In addition to these primary amines, secondary amines may also be used.

Illustrative polybasic acid chlorides include chlorides of malonic acid, succinic acid, adipic acid, maleic acid, isophthalic acid, terephthalic acid, gluconic acid, etc.

Specific examples of the chlorosilane compounds represented by $R_{(4-n)}$—[Si—$Cl_n$ or $R_1'$—Si—$Cl)_m R_{(3-m)}]_n$ in Table 1 or $R_{(4-n)}'$—[Si—$Cl_n$ or $R_2'$—Si—$Cl)_m R_{(3-m)}']_n$ in Table 2 are as follows: dimethyldichlorosilane, methyltrichlorosilane, diethyldichlorosilane, methylethyldichlorosilane, ethyltrichlorosilane, di-n-propyldichlorosilane, methyl-n-propyldichlorosilane, n-propyltrichlorosilane, di-n- butyldichlorosilane, methyl-n-butyldichlorosilane, n-butyltrichlorosilane, di-n-hexyldichlorosilane, methyl-n-hexyldichlorosilane, n-hexyltrichlorosilane, dicyclohexyldichlorosilane, methylcyclohexyldichlorosilane, methyl-n-octyldichlorosilane, diphenyldichlorosilane, methylphenyldichlorosilane, phenyltrichlorosilane, dibenzyldichlorosilane, methylbenzyldichlorosilane, benzyltrichlorosilane, tetrachlorosilane, 1,2-bis(chlorodimethylsilyl)ethane, 1,3-bis(chlorodimethylsilyl)propane, 1,4-bis(chlorodimethylsilyl)benzene, and dichlorotetramethylsiloxane.

Specific examples of the alkoxysilyl isocyanate compounds represented by $(R_1''''O)_n—Si—(NOC)_{(4-n)}$ in Table 1 include the following: methoxysilyl triisocyanate, dimethoxysilyl diisocyanate, ethoxysilyl triisocyanate, diethoxysilyl diisocyanate, isopropoxysilyl triisocyanate, diisopropoxysilyl diisocyanate, n-butoxysilyl triisocyanate, di-n-butoxysilyl diisocyanate, phenoxysilyl triisocyanate, and diphenoxysilyl diisocyanate.

Specific examples of the compounds represented by $R_{(4-n)}—Si(OR_1'—OH)_n$ or $R_1''{\text-}[Si(OR_1'(OH)_mR_{(3-m)}]_n$ in Table 1 or $R_{(4-n)}'—Si(OR_2'—OH)_n$ or $R_2''{\text-}[Si(OR_2'—OH)_mR_{(3-m)}']_n$ in Table 2 are listed below:

CH$_3$—Si$(-$OCH$_2$CH$_2$OH$)_3$, (CH$_3$)$_2$Si$(-$OCH$_2$CH$_2$OH$)_2$,
C$_2$H$_5$—Si$(-$OCH$_2$CH$_2$OH$)_3$, (C$_2$H$_5$)$_2$Si$(-$OCH$_2$CH$_2$OH$)_2$,
CH$_3$(C$_2$H$_5$)$-$Si$(-$OCH$_2$CH$_2$OH$)_2$, $^n$C$_3$H$_7$—Si$(-$OCH$_2$CH$_2$OH$)_3$,
CH$_3$($^n$C$_3$H$_7$)$-$Si$(-$OCH$_2$CH$_2$OH$)_2$, $^n$C$_4$H$_9$—Si$(-$OCH$_2$CH$_2$OH$)_3$,
CH$_3$($^n$C$_4$H$_9$)$-$Si$(-$OCH$_2$CH$_2$OH$)_2$, $^n$C$_6$H$_{13}$—Si$(-$OCH$_2$CH$_2$OH$)_3$,

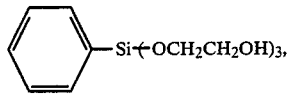

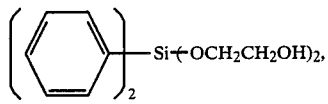

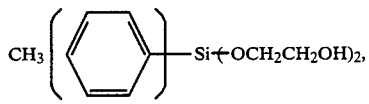

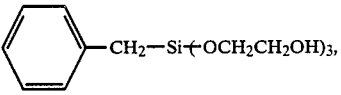

CH$_3$—Si$(-$OCH$_2$CH$_2$CH$_2$OH$)_3$, (CH$_3$)$_2$Si$(-$OCH$_2$CH$_2$CH$_2$OH$)_2$,
CH$_3$—Si$(-$OCH$_2$CH$_2$—O—CH$_2$CH$_2$OH$)_3$,
(CH$_3$)$_2$Si$(-$OCH$_2$CH$_2$—O—CH$_2$CH$_2$OH$)_2$,

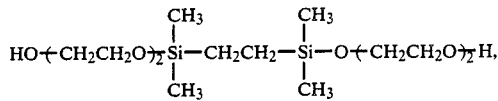

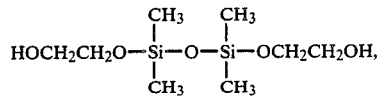

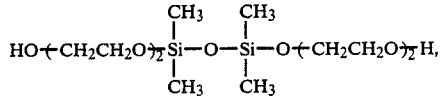

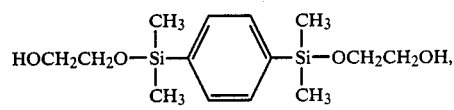

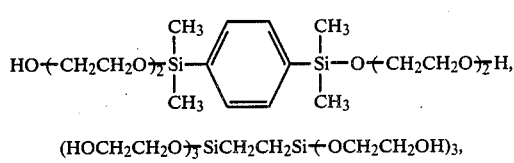

(HOCH$_2$CH$_2$O)$_3$SiCH$_2$CH$_2$Si$(-$OCH$_2$CH$_2$OH$)_3$, (HOCH$_2$CH$_2$O)$_3$Si$(-$CH$_2$)$_4$Si$(-$OCH$_2$CH$_2$OH$)_3$

Among the alkoxysilyl isocyanate compounds above, a compound represented by

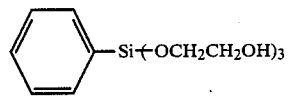

may be prepared by the following proceudres: 4.5 g (1.20 mols) of ethylene glycol and 60.7 g (0.600 mol) of triethylamine are dissolved in 200 ml of methyl ethyl ketone; to this solution, 42.3 g (0.2 mol) of phenyltrichlorosilane in 40 ml of methyl ethyl ketone is added; the mixture is continuously agitated at 50° C. for 3 hours; the resulting precipitate of triethylamine hydrochloride is recovered by filtration and concentrated; excess ethylene glycol is distilled off under vacuum.

Specific examples of the compounds represented by $R_{(4-n)}'—Si(OR_1'OCONHR_1''—NCO_x)_n$ or $R_1'''{\text-}[Si(OR_1'OCONHR_1''—NCO_x)_m—R_{(3-m)}]_n$ in Table 1, or $R_{(4-n)}'—Si(OR_2'OCONHR_2''—NCO_x)_n$ or $R_2'''{\text-}[Si(OR_2'OCONHR_2''—NCO_x)_m—R_{(3-m)}']_n$ in Table 2 include the following:

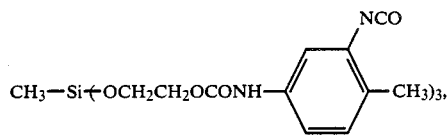

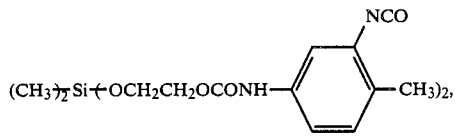

-continued

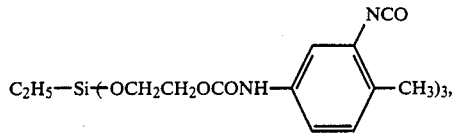
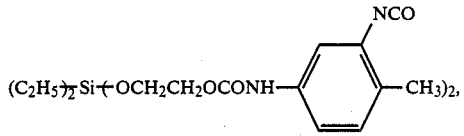
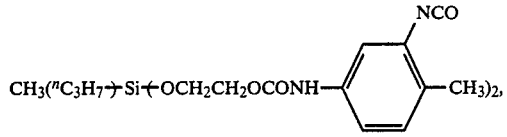
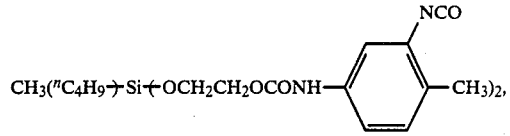
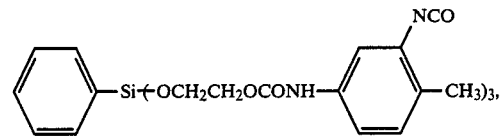
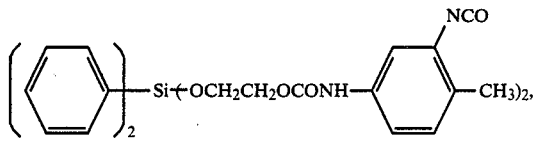
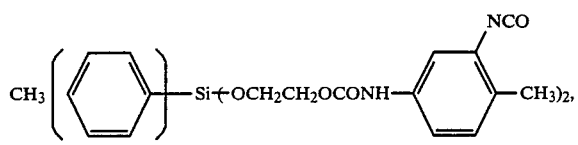
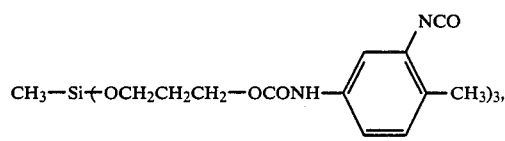

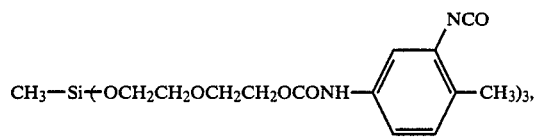

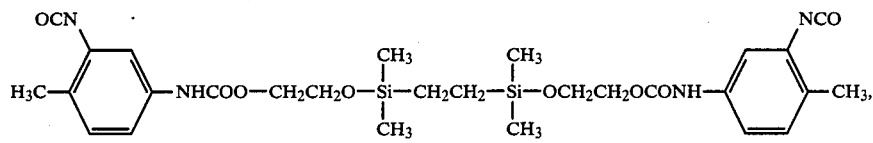

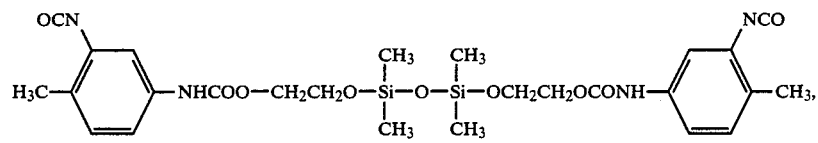

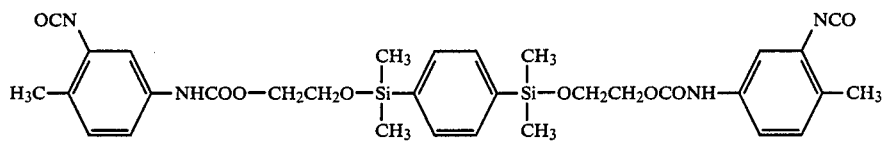

Among these, a compound represented by

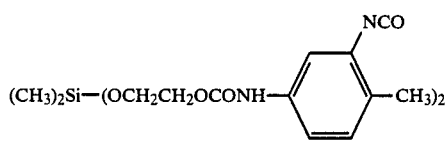

may be prepared by the following specific procedures: $(CH_3)_2$—$Si(OCH_2CH_2OH)_2$ is added to tricresyl phosphate and the mixture is well agitated to form a dispersion; 2,4-tolylene diisocyanate is added to the dispersion at room temperature, and the mixture is agitated for 3 consecutive hours at 60° C. until a colorless transparent solution forms.

Specific examples of the compounds represented by $R_{(4-n)}$—Si—$(OR_1'$—$NH_2)_n$ or $R_1''$—$[Si$—$(OR_1'$—$NH_2)_mR_{(3-m)}]_n$ in Table 1 include the following:

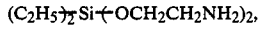
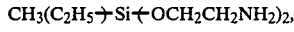

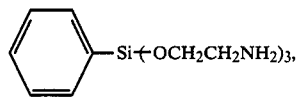

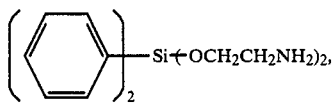

-continued

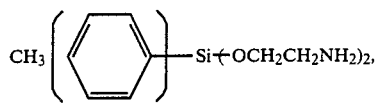

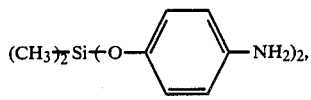

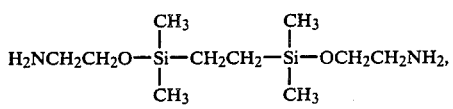

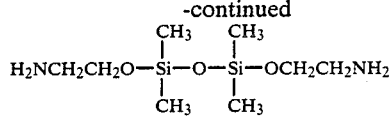

Specific examples of the alkylsilyl isocyanate compounds represented by $R_4'-Si-(NCO)_{(4-n)}$ in Table 2 include methylsilyl triisocyanate, dimethylsilyl diisocyanate, ethylsilyl triisocyanate, diethylsilyl diisocyanate, isopropylsilyl triisocyanate, diisopropylsilyl diisocyanate, n-butylsilyl triisocyanate, di-n-butylsilyl diisocyanate, phenylsilyl triisocyanate, and diphenylsilyl diisocyanate.

Specific examples of the compounds represented by $R_{(4-n)}'-Si-(NHCONHR_2'-OH)_n$ or $R_2''-[-Si-(NHCONHR_2'-OH)_m-R_{3-m})']_n$ in Table 2 include the following:

$CH_3-Si-(NHCONHCH_2CH_2OH)_3$, $(CH_3)_2-Si-(NHCONHCH_2CH_2OH)_2$, $C_2H_5-Si-(NHCONHCH_2CH_2OH)_3$, $(C_2H_5)_2-Si-(NHCONHCH_2CH_2OH)_2$, $CH_3(C_2H_5)-Si-(NHCONHCH_2CH_2OH)_2$, $^nC_3H_7-Si-(NHCONHCH_2CH_2OH)_3$, $CH_3(^nC_3H_7)-Si-(NHCONHCH_2CH_2OH)_2$, $^nC_4H_9-Si-(NHCONHCH_2CH_2OH)_3$, $CH_3(^nC_4H_9)-Si-(NHCONHCH_2CH_2OH)_2$, $^nC_6H_{13}-Si-(NHCONHCH_2CH_2OH)_3$,

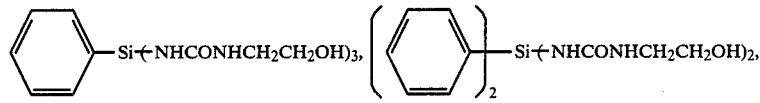

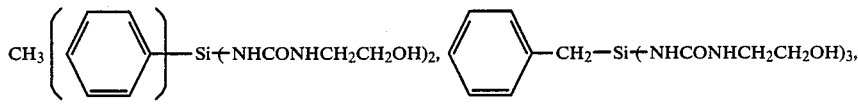

$CH_3-Si-(NHCONHCH_2CH_2CH_2OH)_3$, $(CH_3)_2Si-(NHCONHCH_2CH_2CH_2OH)_2$, $CH_3-Si-(NHCONHCH_2CH_2-O-CH_2CH_2OH)_3$, $(CH_3)_2-Si-(NHCONHCH_2CH_2-O-CH_2CH_2OH)_2$,

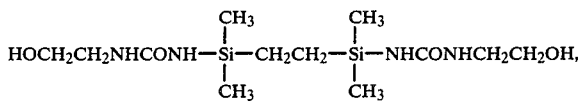

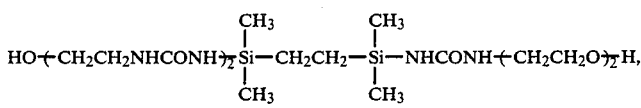

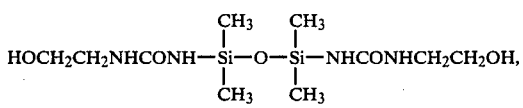

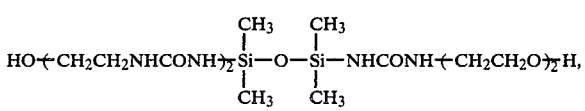

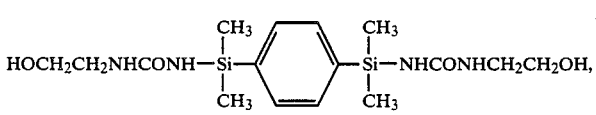

-continued

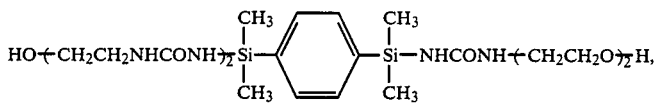

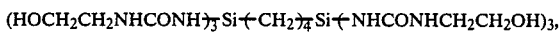

Among these, a compound represented by $(CH_3)_2Si\text{-}(NHCONHCH_2CH_2OH)_2$ may be prepared by the following procedures: 24.5 g of monoethanolamine is stirred in 300 ml of benzene; to the stirred solution, a solution of 28.4 g of dimethylsilyl diisocyanate in 30 ml of benzene is added at room temperature over a period of 30 minutes; the mixture is stirred for 4 consecutive hours and the resulting precipitate of a white solid powder is recovered by filtration, washed and dried to obtain 51.1 g of the end compound.

Specific examples of the compounds represented by $R_{(4-n)}'\text{-}Si\text{-}(NHCONHR_2'OCONHR_2''\text{-}NCO_x)_n$ or $R_2'''\text{-}[Si\text{-}(NHCONHR_2'OCONHR_2''\text{-}NCO_x)_m R_{(3-m)}']_n$ in Table 2 include the following.

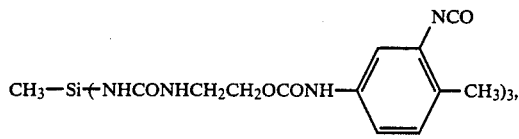

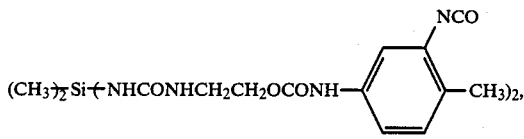

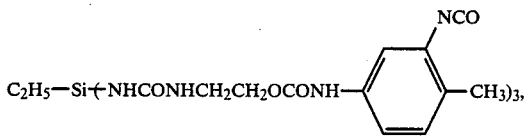

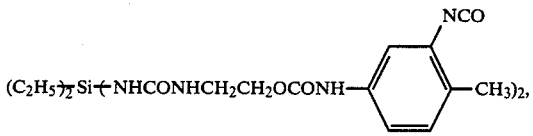

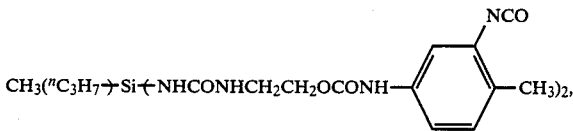

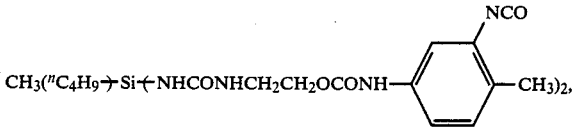

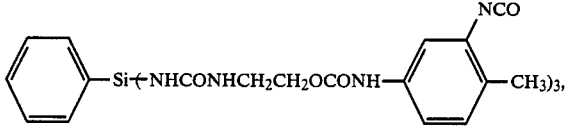

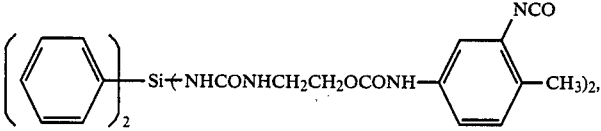

-continued

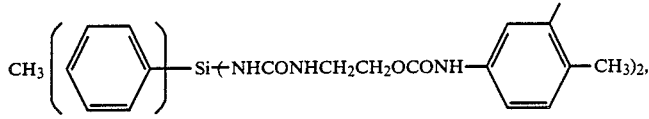

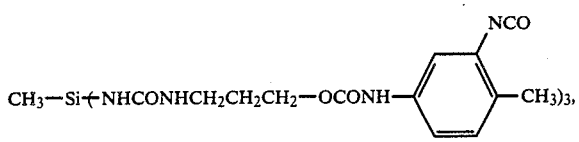

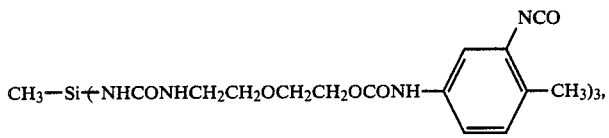

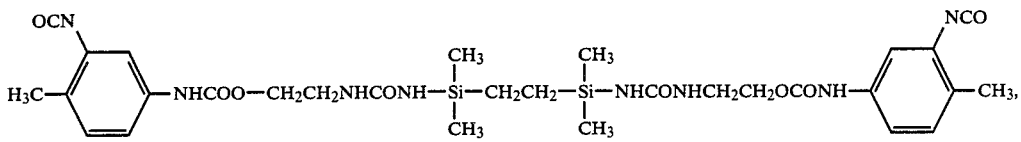

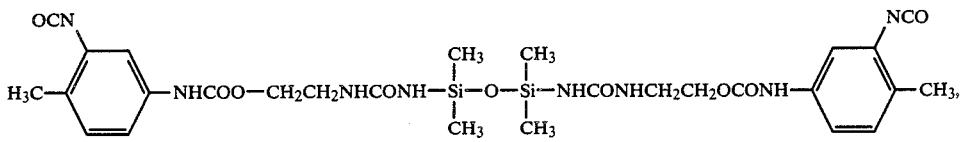

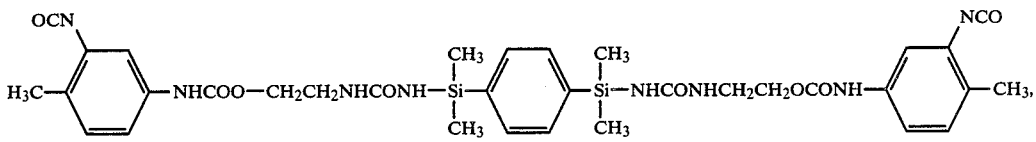

Among these, a compound represented by

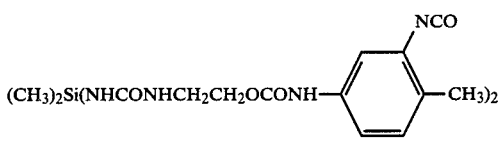

may be prepared by the following specific procedures: (CH₃)₂—Si(NHCONHCH₂CH₂OH)₂ is added to tricresyl phosphate and the mixture is stirred to form a dispersion; 2,4-tolylene diisocyanate is added to the dispersion at room temperature, followed by agitation at 60° C. for 1 hour to obtain a colorless transparent solution.

Specific examples of the compounds represented by $R_{4-n}'$—Si$\pm$NHCONHR$_2'$—NH$_2)_n$ or $R_2''$$\pm$Si$\pm$NH-CONHR$_2'$—NH$_2)_m R_{(3-m)}']_n$ in Table 2 include the following.

CH₃—Si(NHCONHCH₂CH₂NH₂)₃,
C₂H₅—Si(NHCONHCH₂CH₂NH₂)₃,

CH₃(C₂H₅)Si(NHCONHCH₂CH₂NH₂)₂,

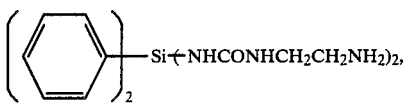

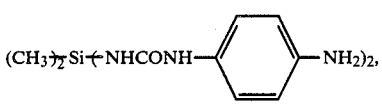

(CH₃)₂Si(NHCONHCH₂CH₂NH₂)₂,
(C₂H₅)₂Si(NHCONHCH₂CH₂NH₂)₂,

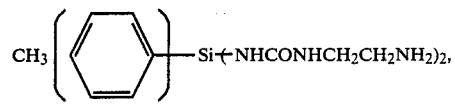

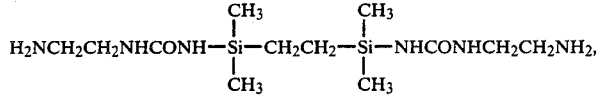

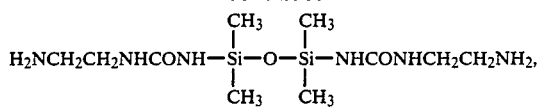

The wall-forming components, A and B, listed in Table 1 may be obtained in either an organic solvent-soluble or water-soluble form by appropriate selection of R, R', R" and R"'.

A microcapsule may be prepared by either interfacial polymerization or in situ polymerization depending upon the solubility of the specific wall-forming components used. If both components are soluble in an organic phase, the in situ polymerization method may be employed to obtain capsules: components A and B are dissolved in an organic phase; the solution is added to an aqueous phase containing a protective colloid and the mixture is stirred to form an emulsion containing fine particles of 1 to 30 μm in size; the emulsion is stirred continuously, with optional heating at 40° to 80° C., whereupon components A and B react with each other to form a polymer within the organic phase; the polymer precipitates at the interface between the organic and aqueous phases to provide microcapsules having a coat of the fine particles of the organic phase. If one of the two wall-forming components, A and B, is soluble in an organic solvent and the other is soluble in an aqueous phase, encapsulation is performed by the interfacial polymerization method: an organic solvent containing either A or B which is the organic solvent-soluble reactive component is added to an aqueous phase containing a protective colloid and the other water-soluble reactive component, and the mixture is agitated to form an emulsion containing fine particles of 1 to 30 μm in size; upon continued stirring with optional heating, the two components A and B react with each other at the interface between the organic and aqueous phases, so as to form a polymer coat at the interface, thereby producing microcapsules containing the emulsified fine particles of the organic solvent phase.

In accordance with these procedures, microcapsules having the wall of a polymer coat containing a silylether or silylureido bond can be produced.

The light-activated acid generator which will be decomposed when the capsule wall containing a silylether or silylureido bond is irradiated by light may be incorporated in the capsule wall if the specific object for which the microcapsules are employed so permits, but usually the acid generator is preliminarily dispersed or dissolved in the organic phase in the capsule.

Many compounds and mixtures thereof are known to be capable of generating acids upon irradiation with actinic radiation, and suitable examples include salts of diazonium, phosphonium, sulfonium or iodonium with $BF_4^-$, $PF_6^-$, $SbF_6^-$, $SiF_6^-$ or $ClO_4^-$, organic halide compounds, orthoquinone diazide sulfonyl chloride, and combinations of organometals/organic halide compounds. Needless to say, the compounds that are described in U.S. Pat. No. 3,779,778 and West German Pat. No. 2,610,842 and which generate acids upon photodecomposition can also be used. Other suitable compounds are those of the type shown in, for example, Japanese Patent Application (OPI) Nos. 77742/80 and 163234/82 (the term "OPI" as used herein refers to a "published unexamined Japanese patent application") which may be combined with suitable dyes such that they provide, upon exposure, a visible contrast between unexposed and exposed areas.

Typical examples of the compounds which are capable of acid generation by photodecomposition are hereunder described in detail.

(1) Trihalomethyl-substituted s-triazine derivatives (VI) or oxadiazole derivatives (V):

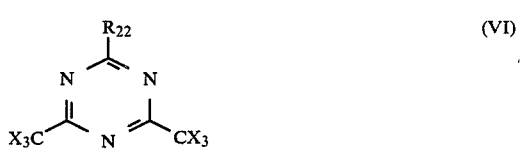

wherein $R_{21}$ is a substituted or unsubstituted aryl or alkenyl group; $R_{22}$ is $R_1$, $-CX_3$ or a substituted or unsubstituted alkyl group; and X is a chlorine or bromine atom.

Specific examples of the compounds (V) and (VI) are listed below:

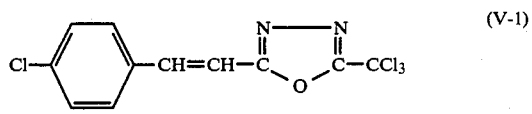

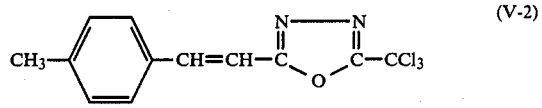

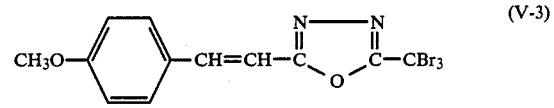

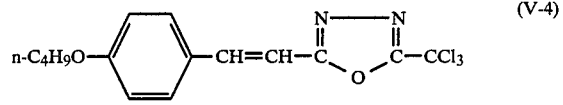

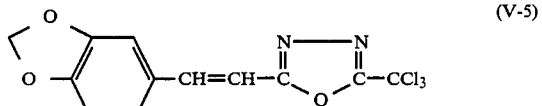

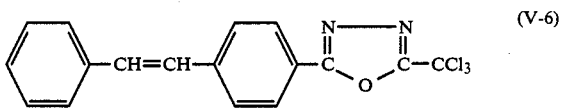

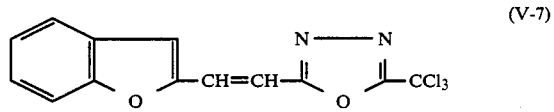

-continued

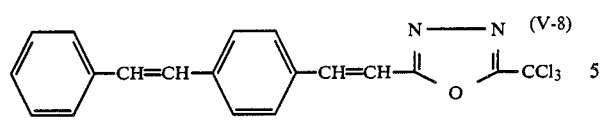 (V-8)

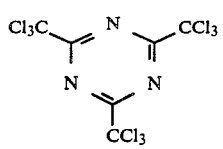 (VI-1)

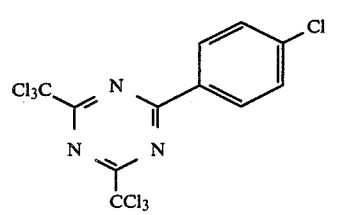 (VI-2)

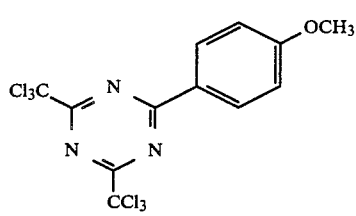 (VI-3)

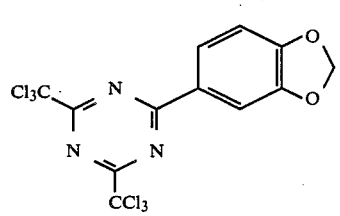 (VI-4)

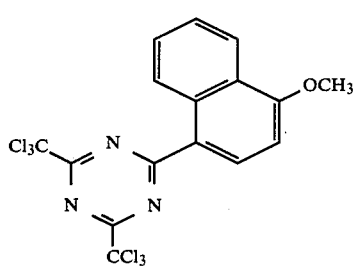 (VI-5)

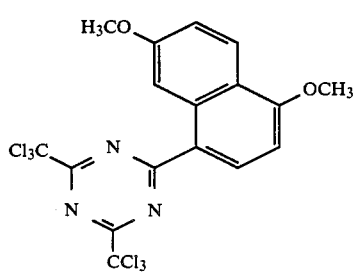 (VI-6)

-continued

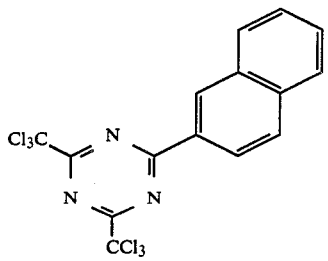 (VI-7)

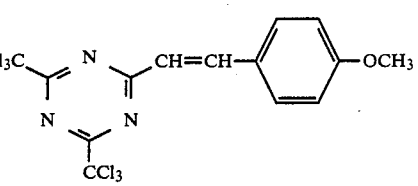 (VI-8)

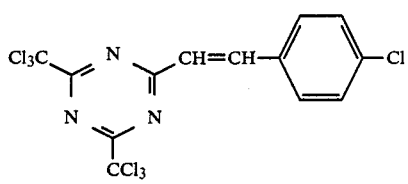 (VI-9)

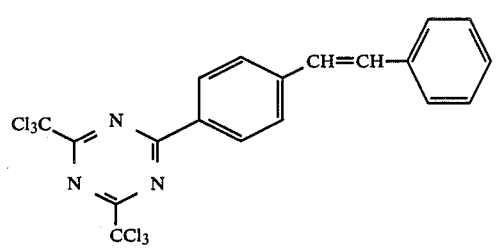 (VI-10)

(2) Iodonium salts (VII) or sulfonium salts (VIII)

 (VII)

 (VIII)

wherein $Ar_1$ and $Ar_2$, which may be the same or different, each represents a substituted or unsubstituted aromatic group; $R_{11}$, $R_{12}$ and $R_{13}$, which may be the same or different, each represents a substituted or unsubstituted alkyl or aromatic group; $X^-$ is $BF_6^-$, $PF_6^-$, $AsF_6^-$, $SbF_6^-$ or $ClO_4^-$; provided that two of $R_{11}$, $R_{12}$, $R_{13}$, $Ar_1$ and $Ar_2$ may be bonded together directly or via a substituent.

Examples of the compounds represented by the general formula (VII) include those which are shown in Japanese Patent Application (OPI) Nos. 158680/85, 100716/76 and Japanese Patent Publication No. 14277/77. Examples of the compounds represented by the general formula (VIII) include those which are shown in Japanese Patent Application (OPI) No. 56885/76, Japanese Patent Publication No. 14278/77, U.S. Pat. No. 4,442,197 and West German Pat. No. 2,904,626.
Specific examples of the compounds (VII) and (VIII) are listed below:
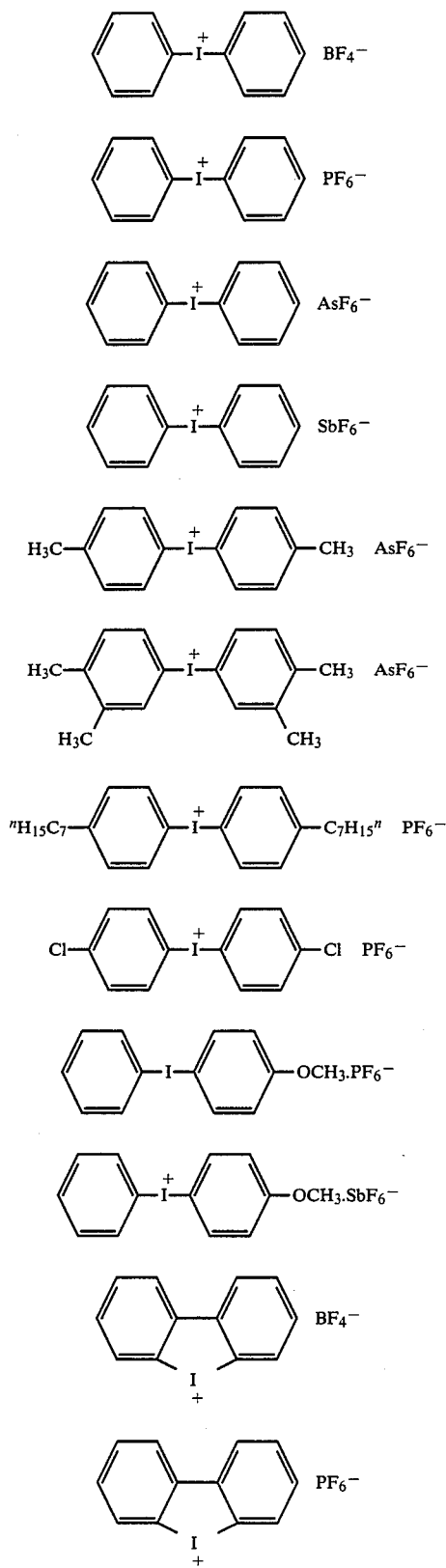
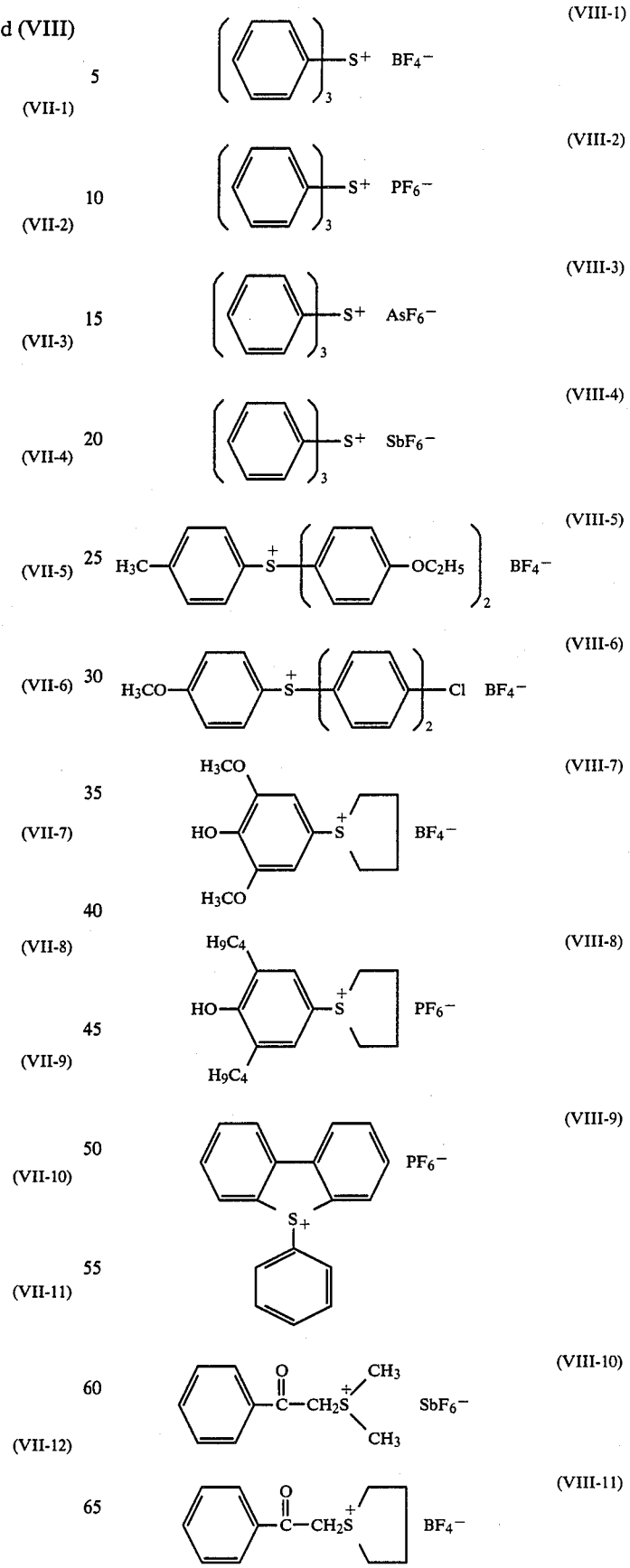

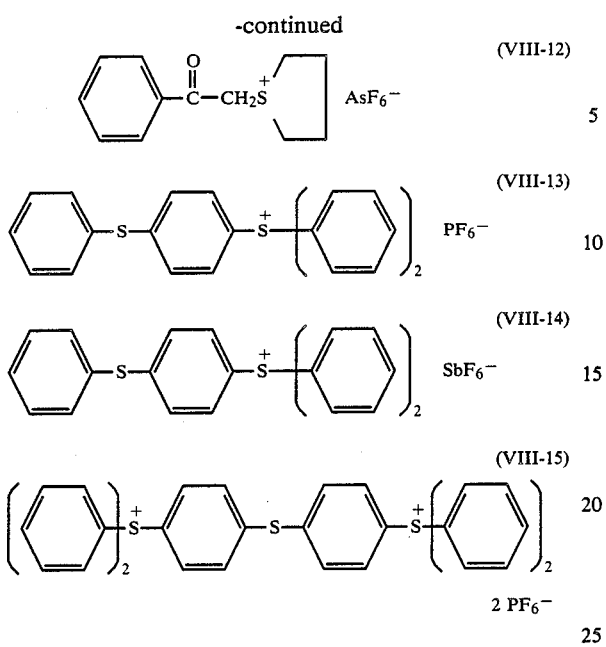

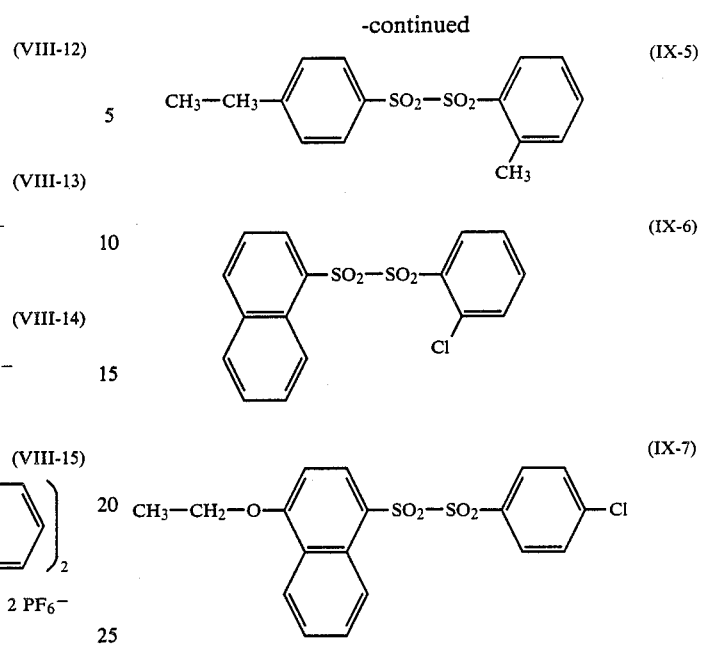

(3) Disulfonic derivatives (IX) or imidosulfonate derivatives (X)

$$Ar_1-SO_2-SO_2-Ar_2 \quad (IX)$$

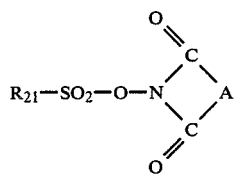
(X)

wherein $Ar_1$ and $Ar_2$, which may be the same or different, each represents a substituted or unsubstituted aryl group; $R_{21}$ is a substituted or unsubstituted alkyl or aryl group; and A is a substituted or unsubstituted alkylene, alkenylene or arylene group.

Specific examples of the compounds (IX) and (X) are listed below:

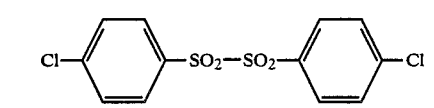

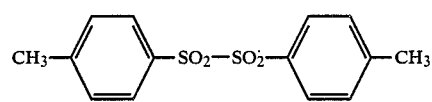

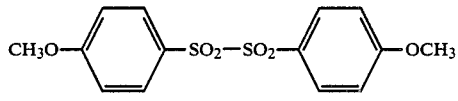

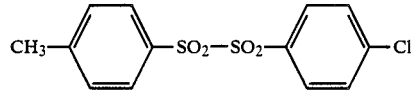

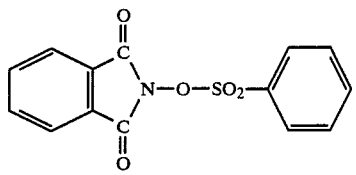

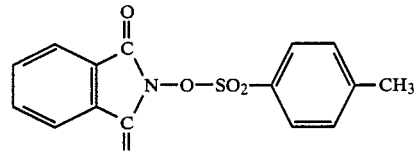

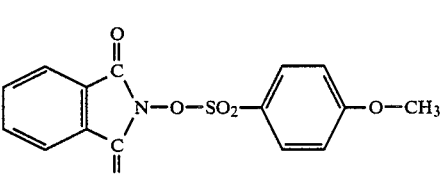

-continued
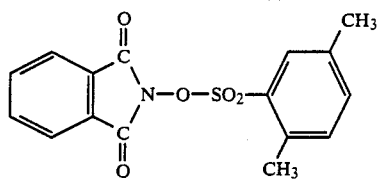 (X-4)
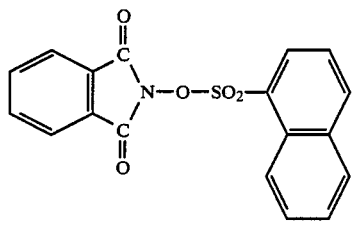 (X-5)
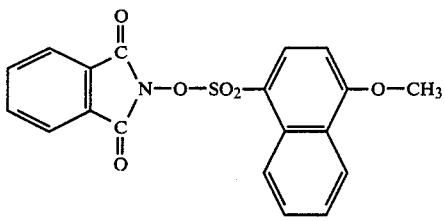 (X-6)
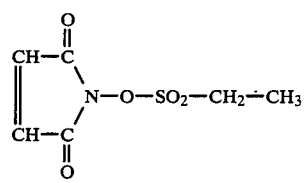 (X-7)
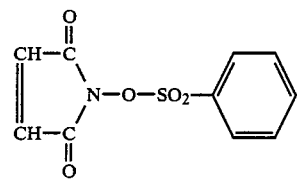 (X-8)
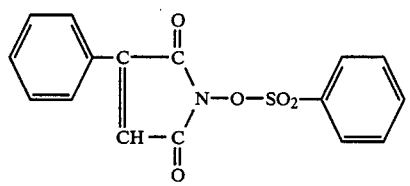 (X-9)
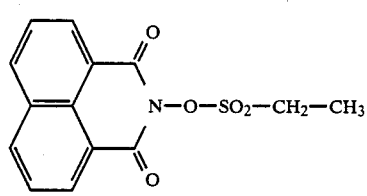 (X-10)
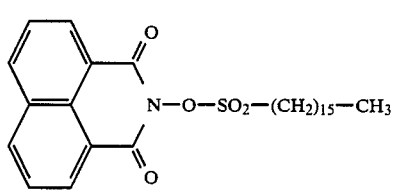 (X-11)
-continued
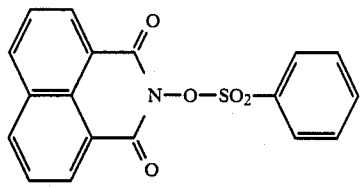 (X-12)
(4) Diazonium salts (XI)
$$Ar-N_2^+X^-  \quad (XI)$$
wherein Ar is a substituted or unsubstituted aromatic group and $X^-$ is an organic carboxylic acid anion, organic sulfonic acid anion, or organic sulfuric acid anion, or $BF_4^-$, $PF_6^-$, $AsF_6^-$, $SbF_6^-$ or $ClO_4^-$.
Specific examples of the compounds (XI) are listed below:
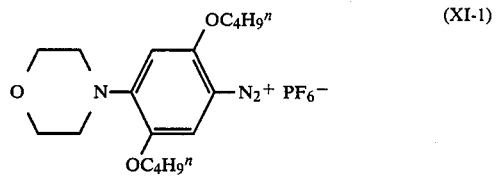 (XI-1)
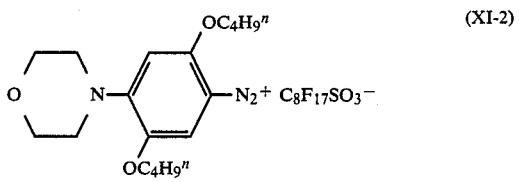 (XI-2)
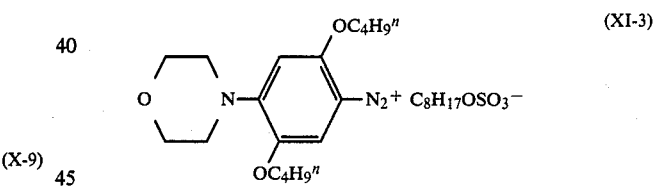 (XI-3)
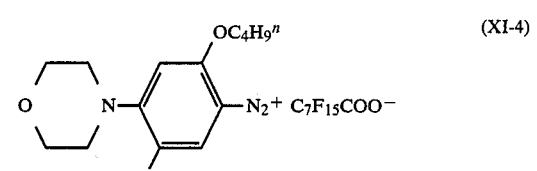 (XI-4)
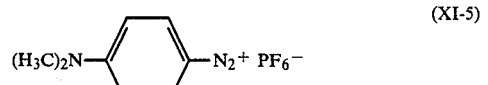 (XI-5)
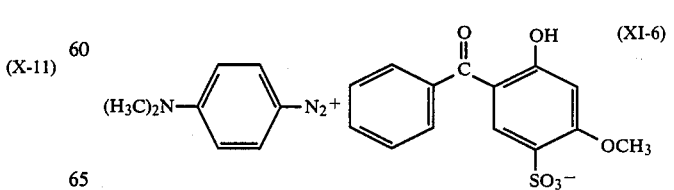 (XI-6)

(XI-7) — structure: phenyl–NH–C6H4–N2+ PF6−

(XI-8) — structure: phenyl–NH–C6H4–N2+ AsF6−

(XI-9) — structure: H3CO–C6H4–NH–C6H4–N2+ PF6−

(XI-10) — structure: H3CO–C6H4–NH–C6H4–N2+ C8F17SO3−

(XI-11) — structure: (H17C8)2N–C6H3(OC2H5)–N2+ PF6−

(XI-12) — structure: H3C–C6H4–S–C6H2(OC2H5)2–N2+ PF6−

(XI-13) — structure: H3C–C6H4–S–C6H2(OC2H5)2–N2+ SbF6−

(XI-14) — structure: Cl–C6H4–N2+ PF6−

(XI-15) — structure: H3CO–C6H4–N2+ PF6−

(XI-16) — structure: C15H31(n)–C6H4–O–C6H4–N2+ BF4−

(XI-17) — structure: 2,4-di-C5H11(t)–C6H3–O–C6H4–N2+ PF6−

(XI-18) — structure: CH3–C4H9CHCONH–C6H4–N2+ PF6−

(XI-19) — structure: H3CO–C6H4–CONH–C6H4–N2+ PF6−

(XI-20) — structure: H3C–C6H4–SO2NH–C6H4–N2+ PF6−

(XI-21) — structure: 2,4-di-C5H11(t)–C6H3–O2CCH2O–C6H4–N2+ · H25C12–C6H4–SO3−

(XI-22) — structure: 2,4-di-C5H11(t)–C6H3–OCH(C2H5)CONH–C6H4–N2+

The compound capable of acid generation by photodecomposition is used in the present invention in an amount which preferably ranges from 0.0001 to 10 mols, more preferably from 0.01 to 2 mols, per mol of the silylether or silylureido group in the microcapsule wall.

If desired, the organic phase in the microcapsule of the present invention may contain a sensitizer, or a compound which enhances the efficiency of acid generation by said acid generating compound under photodecomposition.

While these sensitizers may be used with acid generators of any type, the compounds described in U.S. Pat. Nos. 4,250,053 and 4,442,197 may be used with the acid generators represented by the general formulae (VII) and (VIII). More specifically, the following compounds may be used: anthracene, phenanthrene, perylene, pyrene, chrysene, 1,2-benzanthracene, coronene, 1,6-diphenyl-1,3,5-hexatriene, 1,1,4,4-tetraphenyl-1,3-butadiene, 2,3,4,5-tetraphenylfuran, 2,5-diphenylthiophene, thioxanthone, 2-chlorothioxanthone, phenothiazine, 1,3-diphenylpyrazoline, 1,3-diphenylisobenzofuran, xanthone, benzophenone, 4-hydroxybenzophenone, anthrone, ninhydrin, 9-fluorenone, 2,4,7-trinitrofluorenone, indanone, phenanthraquinone, tetralone, 7-methoxy-4-methylcoumarin, 3-keto-bis(7-diethylaminocoumarin) and Michler's ketone.

These sensitizers are used in amounts which generally range from 0.01 to 20 mols, preferably from 0.1 to 5 mols, per mol of the compound capable of acid generation by photodecomposition.

The acid generator and associated sensitizer are typically dispersed or dissolved in the solvent in a capsule. Suitable solvents include natural mineral oils, animal oils, vegetable oils and synthetic oils. Illustrative mineral oils are petroleum and fractions thereof such as kerosene, gasoline, naphtha and paraffin oil; exemplary animal oils are fish oil and lard; and illustrative vegetable oils are peanut oil, linseed oil, soybean oil, castor oil and corn oil. Exemplary synthetic oils include: biphenyl compounds such as isopropylbiphenyl and isoamylbiphenyl; terphenyl compounds such as the one described in West German Patent Application (OLS) No. 2,153,635; phosphoric acid compounds such as triphenyl phosphate; naphthalene compounds such as the one described in West German Patent Application (OLS) No. 2,141,194; methane compounds such as the one described in West German Patent Application (OLS) No. 2,153,634; phthalic acid compounds such as diethyl phthalate, dibutyl phthalate and dioctyl phthalate; and salicylic acid compounds such as ethyl salicylate.

Volatile solvents may also be used and they include toluene, n-hexane, carbon tetrachloride, butyl acetate and benzene.

Various effective components may be incorporated within the microcapsules of the present invention in accordance with the specific object of their use, and examples of such effective components are color formers which produce a color by reaction, photopolymerizable compositions which polymerize under irradiation by light, agrichemicals, medicines, flavors, various synthetic chemicals, adhesives, liquid crystals, foodstuffs, detergents, dyes, corrosion inhibitors, pigments, and the like.

The basic steps for preparing microcapsules according to the present invention are shown below.

(1) Prepare an aqueous solution containing a water-soluble polymer such as poly(vinyl alcohol), gelatin or carboxymethyl cellulose. In the present invention, the water-soluble polymer is used in an amount which generally ranges from 0.5 to 30%, preferably from 1 to 20%, of the hydrophobic oily solution to be confined in the final capsule. The water-soluble polymer which is used in the present invention may be anionic, nonionic or amphoteric.

(2) A wall-forming, oil-soluble component which is selected from A or B in Table 1 or 2 is dissolved or dispersed in a hydrophobic liquid oil. The amount of this wall-forming component added will vary with the thickness of the wall to be formed and may be selected from the range of 1 to 50 wt% depending upon the specific use of the microcapsule.

(3) Add the hydrophobic solution of (2) to the aqueous solution of water-soluble polymer prepared in (1). Stir the mixture and adjust the size of the emulsified droplets to be within the range of 0.1 to several millimicrons in accordance with the specific object of the use of the microcapsule. In this case, a surfactant which is either anionic, cationic or nonionic may be used as an emulsifier. The obtained emulsified droplets have a size which is substantially equal to that of the desired microcapsule.

(4) The other wall-forming component which is aqueous and selected from A or B shown in Table 1 or 2 is added to the emulsion prepared in (3) after it is dissolved in water. Alternatively, the wall-forming component may be directly added to an aqueous phase. In this case, the wall-forming component may be preliminarily added directly to the aqueous solution prepared in (1).

(5) Stir the mixture with optional heating at 40° to 80° C. so that a polymerization reaction is caused to take place at the interface between the oil and aqueous phases, thereby forming the wall of a microcapsule at said interface.

(6) After encapsulation, optionally filter and repeat washing with water so as to isolate the formed microcapsules.

If the specific use of microcapsules permits, the suspension of microcapsules may be immediately coated onto a support such as a plastic film or cardboard, with a water-soluble binder being added as required.

The size of microcapsules may be appropriately selected in accordance with the specific use of the capsules; it can also be controlled typically by changing the size of the droplets to be obtained in the emulsifying step (3).

If both wall-forming components are soluble in the solvent to be incorporated in a microcapsule, they are either dissolved or dispersed in an oil phase and encapsulation may be achieved by the in situ polymerization method (i.e., microcapsule walls are formed from the oil phase) in substantial accordance with the procedures (1) to (6).

The following examples are provided for the purpose of further illustrating the present invention but are in no sense to be taken as limiting the latter.

EXAMPLE 1

3 g of polyvinyl alcohol (PVA-205 of Kuraray Co., Ltd.; degree of polymerization: 550, degree of saponification: 88 mol%) as a water-soluble polymer was added to 40 g of water and dissolved therein by heating at 80° C. with stirring to obtain a solution of protective colloid. To this aqueous phase solution was added 4 g of $(CH_3)_2 \text{-} Si(OCH_2CH_2OH)_2$ as one capsule wall-forming component and dissolved to form a solution.

To a mixture of 30 g of 1,1-xylylphenylethane (Kureha Chemical Industry Co., Ltd.) as the core component to be confined in microcapsules and 4.0 g of ethyl acetate, 3.0 g of a polyisocyanate (addition product of trimethylpropane and tolylene diisocyanate; Bernock D-750 of Dainippon Ink & Chemicals Inc.) as the other wall-forming component and 1.0 g of a light-activated acid generator having the formula shown below were added and dissolved to make a core solution:

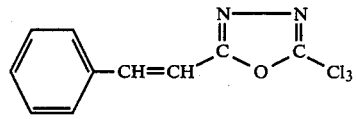

The solution was added to the previously obtained aqueous solution of protective colloid and an O/W emulsion was formed by vigorous agitation, which was continued until the volume average size of the oil droplets decreased to about 8.0 μm.

The resulting emulsion was transferred to a dark place where it was heated at 60° C. with stirring for 8 consecutive hours. The two wall-forming components reacted with each other at the interface between xylylphenylethane and water to form a polymer coat. The resulting microcapsules confined the xylylphenylethane solution of the acid generator.

The microcapsules were separated from the suspension of filtration and, after repeated washing with water, they were dried to obtain 28 g of a microcapsule powder.

A portion (20 g) of the microcapsule powder was added to a heated aqueous solution of dextrin (10 g) and the resulting solution was coated onto a sheet of cardboard (50 g/m²) to provide a deposit of 10 g/m².

The coated sheet was exposed for 5 seconds under an ultrahigh pressure mercury lamp (2 kw) at a distance of 55 cm. It required a pressure of 300 kg/m² to rupture the microcapsules in the unexpected areas but the microcapsules in the exposed areas ruptured easily by application of a pressure of 50 kg/m².

EXAMPLE 2

An aqueous solution of protective colloid was prepared as in Example 1. To this solution, 5 g of hexamethylenediamine was added as one capsule wall-forming component and dissolved.

To 60 g of tricresyl phosphate which was the core material to be confined in a microcapsule, 8 g of the other wall-forming component (which was the addition product of

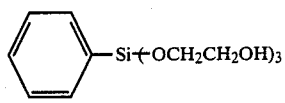

and tolylene diisocyanate), 2.0 g of a light-activated acid generator having the following structural formula:

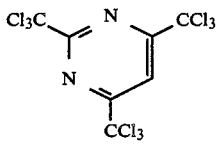

and 0.3 g of a 3-ketocoumarin compound as a light sensitizer were added and dissolved to form a solution.

This solution was added to the previously obtained aqueous solution of protective colloid with vigorous agitation to form an O/W emulsion containing oil droplets of a size of 1 μ. The emulion was heated in the dark at 65° C. for 7 hours with continued stirring to form microcapsules.

After 5 g of SBR latex was added as a binder, the suspension of microcapsules was applied onto a 50 μm thick polyethylene terephthalate base support to form a coat 13 μm thick which was subsequently dried.

As in Example 1, the coated support was exposed for 10 seconds through a filter that would cut off light having a wavelength of 400 nm or below. After exposure, the coated support was treated with toluene; the microcapsules in the unexposed areas remained intact but all of the tricresyl phosphate within the microcapsules in the exposed areas dissolved away in the toluene.

EXAMPLE 3

Water-soluble polymers (2.0 g of gelatin and 1.5 g of carboxymethyl cellulose) were added to 45 g of water and the mixture was heated at 60° C. with stirring to form an aqueous solution of protective colloid. To this solution was added 0.1 g of Turkey red oil as an emulsifier.

To a mixture of 33 g of an alkyl naphthalene (KMC F-113 of Kureha Chemical Industry Co., Ltd.) as the core component to be confined in microcapsules and 4.0 g of ethyl acetate, 3.8 g of the addition product of $(CH_3)_2-Si(OCH_2CH_2OH)_2$ and Millionate MR-100 (methylene bisphenyl isocyanate multimer mixture of Nippon Polyurethane Industry Co., Ltd.) and 1.0 g of Adekaquadrol (ethylenediamine/propylene oxide adduct of Asahi Denka Kagaky K.K.), both being the wall-forming components, and 1.5 g of a light-activated acid generator which was a diazo compound having the formula shown below:

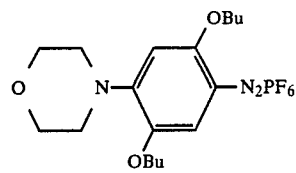

were added and dissolved to form a solution. This solution was added to the previously obtained aqueous solution of protective colloid and an O/W emulsion was formed by vigorous agitation, which was continued until oil droplets having an average size of about 1 μm were obtained. The emulsion was gradually heated to 75° C. in the dark with stirring, which was continued for an additional 3 hours. The wall-forming components in the alkyl naphthalene reacted with each other to form a polymer wall. The resulting microcapsules confined the alkyl naphthalene solution of the acid generator.

The microcapsules were separated from the suspension by filtration and, after repeated washing with water, they were dried to obtain 32 g of a microcapsule powder.

5 g of an electron donating colorless dye precursor (2-anilino-3-chloro-6-diethylaminofluoran) and 10 g of an electron acceptor compound (bisphenol A) were suspended in 150 g of a 5% aqueous solution of polyvinyl alcohol. To the suspension, 15 g of the previously obtained microcapsule powder was added and dispersed therein. The resulting suspension was coated onto a sheet of cardboard to provide a solids deposit of 7 g/m² and the coating was subsequently dried.

The coated sheet was exposed for 4 seconds as in Example 1. No change occurred in the unexposed areas, but the microcapsules in the exposed areas disintegrated and the oil released from within the capsules dissolved both the color former and developer to produce a color image.

EXAMPLE 4

3 g of polyvinyl alcohol (PVA-205 of Kuraray Co., Ltd.; degree of polymerization: 550, degree of saponification: 88 mol%) as a water-soluble polymer was added to 40 g of water and dissolved therein by heating at 80° C. with stirring to obtain a solution of protective colloid. To this aqueous phase solution was added 4 g of $(CH_3)_2-Si-NHCONHCH_2CH_2OH)_2$ as one capsule wall-forming component and it was dissolved to form a solution.

To a mixture of 30 g of 1,1-xylylphenylethane (Kureha Chemical Industry Co., Ltd.) as the core component to be confined in microcapsules and 4.0 g of ethyl acetate, 3.0 g of a polyisocyanate (addition product of trimethylolpropane and tolylene diisocyanate; Bernock D-750 of Dainippon Ink & Chemicals Inc.) as the other wall-forming component and 1.0 g of a light-activated acid generator having the formula shown below were added and dissolved to make a core solution:

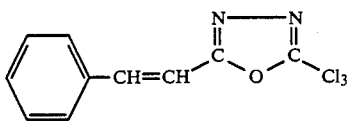

The solution was added to the previously obtained aqueous solution of protective colloid and an O/W emulsion was formed by vigorous agitation, which was continued until the volume average size of the oil droplets decreased to about 8.0 μm.

The resulting emulsion was transferred to a dark place where it was heated at 60° C. with stirring for 8 consecutive hours. The two wall-forming components reacted with each other at the interface between xylylphenylethane and water to form a polymer coat. The resulting microcapsules confined the xylylphenylethane solution of the acid generator.

The microcapsules were separated from the suspension by filtration and, after repeated washing with water, they were dried to obtain 28 g of a microcapsule powder.

A portion (20 g) of the microcapsule powder was added to a heated aqueous solution of dextrin (10 g) and the resulting solution was coated onto a sheet of cardboard (50 g/m$^2$) to provide a deposit of 10 g/m$^2$.

The coated sheet was exposed for 5 seconds under an ultrahigh pressure mercury lamp (2 kw) at a distance of 55 cm. It required a pressure of 300 kg/m$^2$ to be applied in order to rupture the microcapsules in the unexposed areas but the microcapsules in the exposed areas ruptured easily by application of a pressure of 50 kg/m$^2$.

EXAMPLE 5

An aqueous solution of protective colloid was prepared as in Example 1. To this solution, 5 g of hexamethylenediamine was added as one capsule wall-forming component and dissolved.

To 60 g of tricresyl phosphate which was the core component to be confined in a microcapsule, 8 g of the other wall-forming component (which was the addition product of

and toluylene diisocyanate), 2.0 g of a light-activated acid generator having the following structural formula:

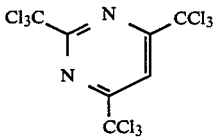

and 0.3 g of a 3-ketocoumarin compound as a light sensitizer were added and dissolved to form a solution.

This solution was added to the previously obtained aqueous solution of protective colloid with vigorous agitation to form an O/W emulsion containing oil droplets of a size of 1 μm. The emulsion was heated in the dark at 65° C. for 7 hours with continued stirring to form microcapsules.

After 5 g of SBR latex was added as a binder, the suspension of microcapsules was applied onto a 50 μm thick polyethylene terephthalate base support to form a coat 13 μm thick which was subsequently dried.

As in Example 4, the coated support was exposed for 10 seconds through a filter that would cut off light having a wavelength of 400 nm or below. After exposure, the coated support was treated with toluene; the microcapsules in the unexposed areas remained intact but all of the tricresyl phosphate within the microcapsules in the exposed areas dissolved away in the toluene.

EXAMPLE 6

Water-soluble polymer (2.0 g of gelatin and 1.5 g of carboxymethyl cellulose) were added to 45 g of water and the mixture was heated at 60° C. with stirring to form an aqueous solution of protective colloid. To this solution was added 0.1 g of Turkey red oil as an emulsifier.

To a mixture of 33 g of an alkyl naphthalene (KMC F-113 of Kureha Chemical Industry Co., Ltd.) as the core component to be confined in microcapsules and 4.0 g of ethyl acetate, 3.8 g of the addition product of $(CH_3)_2$—Si$\leftarrow$NHCONH—$CH_2CH_2OH)_2$ and Millionate MR-100 (methylene bisphenyl isocyanate multimer mixture of Nippon Polyurethane Industry Co., Ltd.) and 1.0 g of Adekaquadrol (ethylenediamine/propylene oxide adduct of Asahi Denka K.K.), both being the wall-forming components, and 1.5 g of a light-activated acid generator which was a diazo compound having the structural formula shown below:

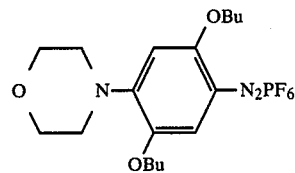

were added and dissolved to form a solution. This solution was added to the previously obtained aqueous solution of protective colloid and an O/W emulsion was formed by vigorous agitation, which was continued until oil droplets having an average size of about 1 μm were obtained. The emulsion was gradually heated to 75° C. in the dark with stirring, which was continued for an additional 3 hours. The wall-forming components in the alkyl naphthalene reacted with each other to form a polymer wall. The resulting microcapsules confined the alkyl naphthalene solution of the acid generator. The microcapsules were separated from the suspension by filtration and, after repeated washing with water, they were dried to obtain 32 g of a microcapsule powder.

5 g of an electron donating colorless dye precursor (2-anilino-3-chloro-6-diethylaminofluoran) and 10 g of an electron acceptor compound (bisphenol A) were suspended in 150 g of a 5% aqueous solution of polyvinyl alcohol. To the suspension, 15 g of the previously obtained microcapsule powder was added and dispersed therein. The resulting suspension was coated onto a sheet of cardboard to provide a solids deposit of 7 g/m$^2$ and the coating was subsequently dried.

The coated sheet was exposed for 4 seconds as in Example 4. No change occurred in the unexposed areas, but the microcapsules in the exposed areas disintegrated and the oil released from within the capsules dissolved both the color former and developer to produce a color image.

While the invention has been described in detail with reference to specific embodiments thereof, it will be apparent to one skilled in the art that various changes and modifications can be made therein without departing from the spirit and scope thereof.

What is claimed is:

1. A photodegradable microcapsule which has a wall made of a polymer coat having an acid-decomposable silyluredo bond represented by the formula

(III)

and which contains a compound that generates an acid upon actinic radiation.

* * * * *